United States Patent
Hack

(10) Patent No.: US 9,211,246 B2
(45) Date of Patent: *Dec. 15, 2015

(54) TREATMENT AND PREVENTION OF DENTAL PATHOLOGY IN HUMANS AND NON-HUMAN ANIMALS

(71) Applicant: Gary David Hack, Columbia, MD (US)

(72) Inventor: Gary David Hack, Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/243,404

(22) Filed: Apr. 2, 2014

(65) Prior Publication Data

US 2014/0212465 A1    Jul. 31, 2014

Related U.S. Application Data

(63) Continuation of application No. 13/417,442, filed on Mar. 12, 2012, now Pat. No. 8,722,080.

(60) Provisional application No. 61/451,676, filed on Mar. 11, 2011.

(51) Int. Cl.

| | |
|---|---|
| A61K 33/42 | (2006.01) |
| A61K 9/14 | (2006.01) |
| A61K 33/00 | (2006.01) |
| A61K 33/08 | (2006.01) |
| A61K 33/16 | (2006.01) |
| A61K 33/22 | (2006.01) |
| A61K 8/55 | (2006.01) |
| A23K 1/175 | (2006.01) |
| A23K 1/18 | (2006.01) |
| A23L 1/304 | (2006.01) |
| A61K 8/19 | (2006.01) |
| A61K 8/24 | (2006.01) |
| A61K 8/25 | (2006.01) |
| A61K 9/00 | (2006.01) |
| A61K 9/16 | (2006.01) |
| A61K 31/663 | (2006.01) |
| A61K 31/675 | (2006.01) |
| A61Q 11/00 | (2006.01) |
| A23L 1/30 | (2006.01) |
| A61K 8/02 | (2006.01) |

(52) U.S. Cl.
CPC ................ *A61K 8/55* (2013.01); *A23K 1/1758* (2013.01); *A23K 1/1846* (2013.01); *A23L 1/30* (2013.01); *A23L 1/304* (2013.01); *A61K 8/02* (2013.01); *A61K 8/19* (2013.01); *A61K 8/24* (2013.01); *A61K 8/25* (2013.01); *A61K 9/0063* (2013.01); *A61K 9/1611* (2013.01); *A61K 31/663* (2013.01); *A61K 31/675* (2013.01); *A61K 33/00* (2013.01); *A61K 33/08* (2013.01); *A61K 33/42* (2013.01); *A61Q 11/00* (2013.01); *A61K 2800/412* (2013.01)

(58) Field of Classification Search
CPC ... A61K 2300/00; A61K 33/08; A61K 33/42; A61K 8/25; A61K 2800/412; A61K 33/00; A61K 33/22; A61K 9/1611
USPC ........... 424/489, 618, 421, 57, 602, 635, 657, 424/692

See application file for complete search history.

(56) References Cited

U.S. PATENT DOCUMENTS

| | | |
|---|---|---|
| 5,658,332 A | 8/1997 | Ducheyne et al. |
| 5,735,942 A | 4/1998 | Litkowski et al. |
| 5,891,233 A | 4/1999 | Salonen et al. |
| 5,906,809 A | 5/1999 | Hack et al. |
| 6,086,374 A | 7/2000 | Litkowski et al. |
| 2004/0052861 A1 | 3/2004 | Hatcher et al. |
| 2009/0208428 A1 | 8/2009 | Hill et al. |

OTHER PUBLICATIONS

Pegoraro et al. Noncarious cervical lesions in adults. Dec. 2005. American Dental Association. vol. 136. pp. 1694-1700.*
FDA. Chapter II Definition 1. Date retrieved: Dec. 18, 2014. p. 1.*
Sigma-Aldrich. Zoledronic acid monohydrate. Date retrieved: Dec. 18, 2014. p. 1.*

* cited by examiner

*Primary Examiner* — Frederick Krass
*Assistant Examiner* — Tracy Liu
(74) *Attorney, Agent, or Firm* — Chalin A. Smith; Smith Patent

(57) ABSTRACT

The present invention relates to methods and compositions for inhibiting, treating, and preventing dental diseases in human and non-human animals, particularly domesticated companion animals. More particularly, the present invention relates to the unexpected discovery that the combination of micron-sized particulate bioactive glass and a topical bisphosphonate yields a composition that is capable of treating and/or preventing dental problems such as periodontal disease, tooth decay and tooth resorption in animals, particularly small mammals such as cats.

26 Claims, 9 Drawing Sheets

BEFORE TREATMENT (5,302X magnification): Dog dentin control surface that has been treated with 37% phosphoric acid for 30 seconds to remove any smear layer after sectioning and grinding to emulate clinical sensitivity. The surface has not been treated with bioactive glass in accordance with the present invention.

BEFORE TREATMENT (10,605X magnification): Dog dentin control surface that has been treated with 37% phosphoric acid for 30 seconds to remove any smear layer after sectioning and grinding to emulate clinical sensitivity. The surface has not been treated with bioactive glass in accordance with the present invention.

AFTER TREATMENT (Particle size range 1-16 microns, 2,454X magnification): A dentin surface that has been treated with an acid etch and treated with a bioactive glass composition in accordance with the present invention in water and glycerin for 2 minutes.

AFTER TREATMENT: (Particle size range 1-16 microns, 2,031X magnification). A dentin surface that has been treated with an acid etch and treated with a bioactive glass composition in accordance with the present invention in water and glycerin for 2 minutes AFTER TREATMENT (Particle size range 1-16 microns, 1,490X magnification): A dentin surface that has been treated with an acid etch and treated with a bioactive glass composition in accordance with the present invention in water and glycerin for 2 minutes.

A dentin surface that has been treated with an acid etch and treated with a bioactive glass composition in accordance with the present invention in water and glycerin for 2 minutes (Particle size range 1-16 microns, 2,634X magnification).

FELINE TOOTH IN AREA OF RESORPTIVE LESION (FORL) (4,016X magnification): Notice breakdown of surface in the pper left corner at Cemento-enamel junction (CEJ) with exposure of underlying dentin.

FELINE TOOTH IN AREA OF RESORPTIVE LESION (FORL) (4,016X magnification): Notice breakdown of surface with exposure of underlying dentin.

FELINE TOOTH IN AREA OF RESORPTIVE LESION (FORL) (4,016X magnification): Notice severe breakdown of surface with exposure of underlying dentin.

TREATMENT AND PREVENTION OF DENTAL PATHOLOGY IN HUMANS AND NON-HUMAN ANIMALS

PRIORITY

This application is a continuation of U.S. patent application Ser. No. 13/417,442 filed Mar. 12, 2012, which, in turn, claims the benefit of U.S. Provisional Application Ser. No. 61/451,676 filed Mar. 11, 2011, the contents of which are incorporated by reference herein.

FIELD OF THE INVENTION

The present invention relates to compositions and methods for inhibiting, treating, and preventing dental pathology in humans and non-human animals, particularly domesticated companion animals such as dogs and cats.

BACKGROUND TO THE INVENTION

Tooth and gum disease can lead to serious health problems both in humans and companion animals. However, dogs and cats make use of their teeth more than humans do. Accordingly, toothache, dental disease, and loss of teeth can all have serious consequences for companion animals. To date, damage to the teeth and gums in companion animals is considered to be permanent and irreversible. According to the American Veterinary Dental Society, 80% of dogs and 70% of cats have periodontal (gum) disease by the age of three. Proper dental care could increase the life of these animals by many years. Accordingly, maintenance of good oral health and prevention of oral disease is a primary necessity for animals, that, unlike humans, do not have the ability to exercise control over oral and dental hygiene by using proper preventative techniques.

Dental care in dogs and cats has become common. Like humans, dog teeth and gums are also susceptible to many of the same oral health problems (e.g., gingivitis and periodontal disease). However, unlike humans, animals rarely get cavities. This is because cavities are primarily caused by the high sugar content of the human diet and the morphology of human teeth. However, periodontal disease affects both human and mammals alike. Bacteria and plaque that attaches to the tissues of the mouth can cause periodontal disease. The first stage of periodontal disease is gingivitis, which is very common. In this stage, the bacteria have mixed with saliva and formed plaque. Plaque adheres to the teeth and hardens, forming tartar and calculus. These tartar deposits irritate the gum tissue and cause inflammation, swelling, and infection. It is at this stage that gingivitis is most notable.

There are indications that oral health status has a profound effect on an animal's general health. Periodontal disease and other oral cavity pathologies may cause bacteria and/or their toxins to enter the bloodstream with potentially deleterious effects on various internal organs (e.g., the heart, kidneys, liver, etc.). Conversely, poor systemic health may manifest in the oral cavity in various ways and may also exacerbate periodontal disease. An animal's dental examination is therefore not always limited to the oral cavity, but frequently includes a general physical examination. Laboratory examinations, to evaluate systemic disease concerns, are also commonly performed. Some dogs and cats suffer from chronic oral infection (e.g., stomatitis, a poorly understood condition that is difficult to treat) and oral cancer.

Pathologic dental conditions are also common in animals, particularly cats. Examples of pathologic dental conditions in felines may include such conditions as tooth lesions. Common tooth lesions found in cats include Feline Odontoclastic Resorptive Lesions (FORL) and dental fractures. Other common oral conditions observed in the cat include periodontal disease (gingivitis, periodontitis), and feline gingivitis/stomatitis syndrome (lymphocytic-plasmacytic gingivitis stomatitis (LPGS), a severe inflammatory condition). The lesions of feline gingivitis/stomatitis syndrome may include inflammation of periodontal structures, oral mucosa, lips and/or tongue.

Plaque bacteria on the teeth may cause periodontal disease. The combined effects of bacterial toxins and the products of the host's inflammatory response to the bacteria may cause the periodontal tissues to become inflamed. Periodontal tissues may be damaged and/or destroyed if intervention does not occur. An unusually aggressive response by a subject's immune system may explain why some individual patients or certain breeds of cats exhibit rapidly progressing and more severe disease.

FORL (otherwise commonly referred to as neck lesions, cervical line erosions, and/or cat cavities) is the most common dental problem in seen in cats. Studies worldwide have shown incidence rates in cats of dental problems of up to 75%. FORL is a very painful condition. Clinical signs associated with FORL may include anorexia, drooling, refusal to eat, and/or malaise.

Another condition associated with the oral health of, for example cats, is feline gingivitis/stomatitis syndrome (FGS). Cats with FGS may have clinical signs of partial to complete anorexia, drooling, halitosis, and/or oral pain. Physical exams of felines may evidence signs of gingivitis (inflammation of the gingiva), stomatitis (inflammation extending to the oral mucosa), palatitis, faucitis (inflammation of the caudal fauca), glossal ulceration, pharyngitis, and/or submandibular lymphadenopathy (swollen glands).

Additional oral maladies may include and/or are a result of, for example, feline calicivirus (FCV). FCV is a virus of the family Caliciviridae that is believed to cause disease in cats. FCV can be isolated from about 50 percent of cats with upper respiratory infection.

Animals infected with FCV may develop symptoms acutely, chronically, or not at all. Latent infections may become symptomatic when the animal is stressed. Acute symptoms of FCV include fever, conjunctivitis, nasal discharge, sneezing, and/or ulceration of the mouth (stomatitis). Stomatitis may develop without any upper respiratory infection symptoms, but fever and loss of appetite may occur. The great variability of symptoms in individual cases of FCV may be related to the existence of different strains of the virus.

With many of the oral maladies (especially those mentioned above typically associated with felines) there is little recourse available to the pet owner. If an oral malady is diagnosed early enough, aggressive and regular oral cleaning may (but not necessarily) eventually clear up the malady. A veterinarian and/or pet owner may have to clean the pet's oral cavity several times a week for months or for the duration of the animal's life. Many times, especially if the malady is not diagnosed early enough, the only recourse available is oral surgery including, for example, extracting any affected teeth. However, even full tooth extraction does not always clear up certain pathological conditions (e.g., chronic ulcerative paradental stomatitis (CUPS)), which is a painful condition seen in dogs and cats.

Therefore, there is a need for compositions and methods for maintaining good oral health as well as preventing and treating oral disease in companion animals.

SUMMARY OF THE INVENTION

Given the above described need in the art, it is a goal of the present invention to provide compositions and methods that inhibit, ameliorate or reduce the severity of dental pathology both in humans and companion animals, examples of which include but are not limited to, dental resorptive diseases such feline osteoclastic resorptive lesions (FORL), plaque accumulation, periodontal disease, gingivitis, periodontitis inflammation, exposed and opened dentinal tubules, dentinal hypersensitivity, cavities, and the like. More particularly, the present invention relates to compositions and methods for the treatment and/or prevention of dental disease and/or tooth resorption in companion animals, more particularly compositions comprising a therapeutically effective amount of a particular bioactive glass, formulated with or without a topical agent and optionally including at least one bisphosphonate, formulated for direct delivery to the teeth and/or surrounding tissues. Specific objectives and embodiments of the invention are as follows:

It is an object of the present invention to provide compositions and methods for treating, preventing or reducing the risk of contracting dental resorptive lesions in mammals, such as humans and companion animals, by administering to a suitable subject in need thereof a composition comprising micron-sized particulates of bioactive glass to include dentinal tubule occluding sizes, or a pharmaceutically acceptable salt thereof, preferably in combination with at least one bisphosphonate.

It is a further object of the present invention to provide methods for inhibiting dental resorptive lesions in cats by administering to a suitable subject in need thereof a composition comprising a micron-sized particulate of bioactive glass or a pharmaceutically acceptable salt thereof, preferably in combination with at least one bisphosphonate.

It is yet another object of the present invention to provide methods for alleviating the pain associated with dental resorptive lesions in mammals by administering to a suitable subject in need thereof a composition comprising micron-sized particulates of bioactive glass to include dentinal tubule occluding sizes, or a pharmaceutically acceptable salt thereof, preferably in combination with at least one bisphosphonate.

It is yet another object of the present invention to provide methods for reducing the risk of tooth loss associated with dental resorptive lesions in mammals by administering to a suitable subject in need thereof a composition comprising a bisphosphonate or a pharmaceutically acceptable salt thereof, preferably in combination with micron-sized particulates of a suitable bioactive glass, more preferably bioactive glass particulates sized to occlude dentinal tubules.

It is yet a further object of the present invention to provide methods for selectively delivering a therapeutically effective amount of a bisphosphonate or a pharmaceutically acceptable salt thereof, preferably in combination with micron-sized particulates of a suitable bioactive glass, more preferably bioactive glass particulates sized to occlude dentinal tubules, to the tooth surface, more preferably the subgingival tooth surface as well as alveoli dentales.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims.

BRIEF DESCRIPTION OF THE DRAWINGS

Various aspects and applications of the present invention will become apparent to the skilled artisan upon consideration of the brief description of the figures and the detailed description of the present invention and its preferred embodiments that follows.

DETAILED DESCRIPTION OF THE PREFERRED EMBODIMENTS

Figure 1:
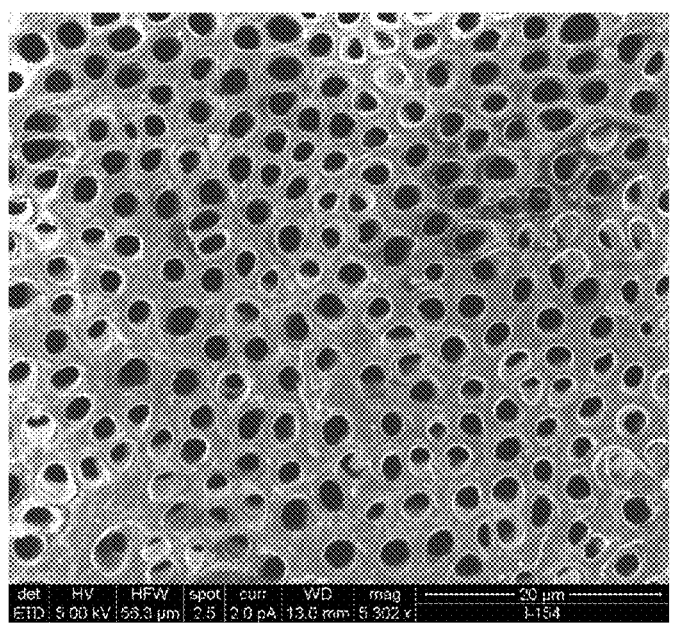
FIG. 1 depicts a dog dentin control surface that has been treated with 37% phosphoric acid for 30 seconds to remove any smear layer after sectioning and grinding to open the dentinal tubules emulating clinical sensitivity and FORL. The surface has not been treated with bioactive glass in accordance with the present invention (5,302× magnification).

The present invention relates to the unexpected discovery that the combination of micron-sized particulates of bioactive glass, especially dentinal tubule occluding particulates, and a topical bisphosphonate yields a composition that is capable of treating and/or preventing dental problems such as periodontal disease, tooth decay and tooth resorption in human and non-human mammals, particularly small mammals such as cats. This novel combination augments the natural healing process. The therapeutic effects of the combination of the present invention are most dramatically illustrated in the domestic cat, for example in the context of the treatment of Feline Osteoclastic Resorptive Lesions (FORL). However, the compositions and methods of the present invention may be applied to other mammals as who experience analogous dental pathologies. The compositions and methods of the present invention may also be directed to the treatment and prevention of noncarious cervical lesions (NCCLs).

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs, in accordance with conventional usage. To that end, definitions of common terms in molecular biology may be found, for example, in Benjamin Levin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references. However, in case of conflict, the present specification, including definitions, will control. Accordingly, in the context of the present invention, the following definitions apply:

DEFINITIONS

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a oral cavity disease), in which case treating refers to administering to a subject (including, for example, a dog or cat in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the subject's condition, but may not be a complete cure of the pathological condition. In other certain aspects of the invention, those in need thereof of treatment include, those in which a pathological condition of the invention (including, for example, an oral cavity disease) is to be prevented, in which case treating refers to administering to a subject a therapeutically effective amount of a composition to a subject (including, for example, a dog or cat in need of treatment) at risk of developing a pathological conditional of the invention.

In the context of the present invention, the terms "subject" and "patient are interchangeably used to refer to human and non-human animals, especially mammals undergoing the described therapy. Preferred mammals are small domesticated animals, particularly companion animal and pets, including but not limited to, mice, rats, hamsters, guinea-pigs, rabbits, cats, and dogs, and the like. Certain of the described therapies also find application to humans.

As used herein, the term "plaque" means sticky material that develops on and around the exposed portions of teeth, consisting of material such as bacteria, mucus and food debris. The term "plaque build-up" means plaque that remains on the teeth after one or more routine brushings of the teeth.

As used herein, the term "preventing plaque" means reducing, inhibiting and/or precluding the development of plaque on and around the teeth, including both exposed and subgingival portion, or reducing or inhibiting the risk of plaque forming on portions of teeth.

As used herein, the term "reducing plaque" means decreasing or lessening the amount of plaque forming on and around portions of teeth.

As used herein, the term "preventing plaque build-up" means limiting, inhibiting, and/or precluding the development of plaque which remains on teeth after one or more routine brushings of the teeth or reducing the risk of plaque remaining on the teeth after one or more routine brushings of the teeth.

As used herein, the term "reducing plaque build-up" means decreasing or lessening the total amount of plaque remaining on one or more teeth after one or more routine brushings of the teeth.

As used herein, "gingivitis" means inflammation of the gums or gingiva due to bacteria-containing plaque on one or more adjacent teeth.

As used herein, "preventing gingivitis" means precluding the development of inflammation of the gums or gingiva due to bacteria-containing plaque on one or more adjacent teeth or reducing the risk of inflammation of the gums or gingiva due to bacteria-containing plaque on one or more adjacent teeth.

As used herein, "reducing gingivitis" means decreasing or lessening any inflammation of the gums or gingiva due to bacteria-containing plaque on one or more adjacent teeth.

As used herein, the term "non-aqueous" means anhydrous or substantially free of water. The individual components of the non-aqueous composition may contain limited amounts of water as long as the overall composition remains substantially free of water.

As used herein, the term "dentifrice" includes any preparation used in maintaining oral hygiene, particularly for cleansing all or a portion of the oral cavity of an individual. The dentifrice may be a dentist- or patient-applied solid or semi-solid, e.g., a dissolvable or absorbable film, paste, powder, gum, floss or composite, a liquid or suspension, e.g., a solution, rinse, sealant, or varnish, or a combination thereof, such as a gel, or mousse, and encompasses both permanent and transient products such as sealants and varnishes.

As used herein, the term "toothpaste" includes any semi-solid patient- or professional-applied dentifrice preparation presented in the form of a paste, cream or gel specially prepared for cleaning the surfaces of teeth.

As used herein, the term "oral cavity" means an individual's teeth, and gums, including all periodontal regions including teeth down to the gingival sulcular crevice and/or the base of the periodontal pockets.

As used herein, the term "average particle size" in general means that some particles will be smaller and some particles will be bigger than the size specified. For purposes of this application and by way of example, where a non-aqueous composition contains bioactive glass particles of an average particle size of less than about 10 microns, typically 90-95% of the particles will be less than about 20 microns. Where the non-aqueous composition contains bioactive glass particles of an average particle size of less than about 5 microns, typically 90-95% of the particles will be less than about 15 microns. Where the non-aqueous composition contains bioactive glass particles of an average particle size of less than about 2 microns (i.e., a dentinal tubule-occluding size), typically 90-95% of the particles will be less than about 6 microns.

In the context of the present invention, the terms "bioactive glass" or "biologically active glass" are used interchangeably to refer to an inorganic glass material having an oxide of silicon as its major component and that is capable of bonding with growing tissue when reacted with physiological fluids. Bioactive glass interacts with the body's tissues to stimulate cell growth and provide vital anti-bacterial, structural and/or regenerative properties. By way of example, a bioactive glass in accordance with the invention is a glass composition that will form a layer of hydroxycarbonate apatite in vitro when placed in a simulated body fluid. A bioactive glass suitable for use in connection with the present invention must be non-toxic, resorbable and biocompatible such that it does not trigger an overwhelmingly adverse immune response in the body, such as in the oral cavity. Preferred bioglass materials are fabricated by a sol-gel process, have a high silicon and a low nitrate content, can be provided as a solid or a powder and can easily be combined with gels and sprays. Illustrative examples, are described in detail below and include TheraGlass® compositions (TheraGlass Limited, London, UK), with and without the addition of silver.

Periodontal Disease in Companion Animals:

The American Veterinary Medical Association (AVMA) encourages all owners of dogs and cats to regularly brush their pet's teeth and see their veterinarian for regular dental checkups. Veterinarians report that periodontal disease is the most commonly diagnosed problem in cats and dogs. Periodontal disease can lead to painful infections of the mouth, and in severe cases these infections can spread and become life-threatening conditions. Oral disease is the number one problem in companion animals. Through knowledge and early detection, veterinarians can improve the quality of an animal's health and extend their life expectancy. This invention is designed to treat and/or prevent oral disease leading to unnecessary oral pain and disease.

Periodontal disease affects 85% of both cats and dogs over the age of 2 years. As the bacterial plaque and tartar accumulate on the tooth surface, it's waste products release toxins, which damage the gums and supporting bone structures. In the early stages, the gums start to redden and become swollen. This is called gingivitis. The process leads to bad breath in the animals called halitosis. If a thorough dental cleaning by a dental veterinarian is done at this stage the disease can be reversed and the gums return to normal. If no treatment is done, the disease progresses and the gums become more inflamed, bleed and start to recede away from the teeth exposing the root surface which can lead to exposed dentinal tubules and dentinal hypersensitivity or tooth sensitivity, and, in worst case scenarios, FORL. Further deterioration leads to a breakdown of the tooth's supporting bone and ligaments. These supporting structures are further damaged by bone destruction. This is called periodontitis or inflammation of the supporting structures of the tooth. In certain breeds (including, for example, Cocker Spaniels, Dobermans, Maine Coon Cats and Abyssinians), the inflammation caused by gingivitis can also lead to the gums enlarging and overgrowing the teeth. This is called gingival hyperplasia. The overgrowth creates a pseudo-pocket around the tooth that traps even more debris and bacteria. The result is an increase of infection and pus below the gum line. The veterinary dentist can only restore the normal height of the gingiva by surgery. This procedure, also called a gingivectomy, utilizes high frequency radio waves to cut the gums, reduce bleeding, and diminish pain. It will not only eliminate the pocket, but also restores the mouth's self-cleaning mechanism and reduces the speed of further plaque and tartar accumulation under the gum line. In addition to the significant local effects in the mouth of pain and inflammation, there are also significant systemic effects on the animal. Bacteria from periodontal disease can enter the bold stream and have a negative impact on the animal's kidneys, heart, lungs, liver, pancreas, muscles, and even the brain.

Tooth Decay in Companion Animals:

Interestingly, tooth cavities in dogs were once thought not to develop. Veterinarians are now diagnosing tooth decay and cavities with an increasing frequency in dogs. With routine oral exams and the routine use of dental radiographs in veterinary medicine, the diagnosis of tooth cavities is clearly increasing.

The earlier these lesions are diagnosed the greater the ability to save rather than extract these teeth. Early cavities involve damage to tooth enamel and dentin. Longer-term tooth decay results in pulp inflammation, infection, discoloration and death of the tooth. These teeth must be treated by root canal therapy or by dental extraction. Some teeth fracture due to extensive tooth destruction. The problem may progress to facial swelling and abscess formation.

Carious lesions are most frequently identified on the occlusal, biting, or chewing surfaces of molar teeth in dogs. Early lesions are diagnosed by observation and investigation of discolored areas of teeth. Soft enamel may be detected using an explorer probe. These lesions progress into the dentin. The dentin is demineralized by the decay process. Dental radiographs confirm the presence and the extent of these lesions. Early tooth decay in dogs is detected with the explorer probe as soft enamel and dentin. It is essential to take and evaluate dental radiographs before deciding to treat or to extract these teeth. If the tooth is non-vital it may be treated by root canal therapy and then with a restoration. Carious lesions may be restored by performing "cavity preparation" and the placement of amalgam or composite restorations (fillings).

Pulpal Infection and Lesion Formation in Mammals:

Numerous studies have shown that bacteria are the main etiologic agent of pulpal infection and periradicular lesion formation. The most frequent route of infection is the progression of the carious lesion into the pulp. Other routes of pulpal infection include cracks, trauma, periodontal pockets. The primary bacterium associated with dental caries is *Strep-*

*tococcus mutans.* However, bacteria associated with deep caries and advanced root carious lesions belong to the group of Gram-positive cocci and rods, and are dominated by *streptococci, lactobacilli* and *Actinomyces*. On the other hand, the microbial flora of infected root canals is polymicrobial in nature and is dominated by Gram-negative anaerobes. Therefore, microbial selection occurs within the root canal ecosystem associated with infections of endodontic origin. Studies on endodontic prognosis have demonstrated that the presence of residual bacteria at the time of root canal completion (obturation) is associated with significantly higher rates of treatment failure. In addition, endodontically treated tooth is vulnerable to recontamination from the oral cavity. Therefore, the endodontically treated tooth is vulnerable to treatment failure due to the residual infection as well as the re-infection of the root canal system.

With the currently available root filling materials, even an ideally obturated root canal is susceptible to re-infection by microorganisms introduced into the system via coronal leakage. The commonly used root filling material, gutta percha, does not adhere to dentin in the absence of root canal sealer. Therefore, the sealer is necessary to prevent leakage along the gutta percha and dentin interface to prevent ingress of the bacteria from the oral environment to the periapical tissues. In addition, the sealer is also more likely to come in direct contact with the remaining viable microorganisms in the dentinal tubules and undebrided parts of the root canal system.

It is known that certain metal ions have a negative influence on bacterial enzymatic functions, e.g. silver ions inhibits fructosidase from *Streptococcus mutans*, or on cellular processes like the adaptive response caused by DNA damaging processes as demonstrated for *Escherichia coli* and cadmium/mercury ions. Although the efficacy of silver ions as anti-infection and anti-contamination agent is well established, the mechanism by which the silver ions exert its antibacterial activity is not yet fully understood. Silver ions have been shown to have broad-spectrum antibacterial and antifungal activity, and also work well under anaerobic conditions. Silver ions have also been shown to destabilize biofilm structures allowing for increased susceptibility of the bacteria to antimicrobial agents. Silver ions have been placed in endodontic sealers for its slow releasing antimicrobial activity.

Silver ions nonspecific antimicrobial activity may be utilized to improve the microbiocidal efficacy of endodontic sealers against the remaining bacteria in the root canal system that survives rigorous chemo-mechanical treatment. Bacterial re-infection of the root canal system after endodontic treatment may also be retarded by the continual release of silver ions from the root canal sealer.

Microorganisms that infect root canals may adhere to the dentinal wall or penetrate deeper into dentinal tubules, whereas the bacteria that adhere superficially to the root canal walls are more likely to be eradicated by chemo-mechanical debridement. However, bacteria that infect dentinal tubules and remain in undebrided parts of the root canal system may be susceptible to the antimicrobial components leaching from the sealer. Therefore, root canal sealers with excellent adhesion to dentin and sustained antibacterial activity are desired to entomb and/or kill the microorganisms that survive chemo-mechanical debridement.

Unfortunately, the silver-containing endodontic sealers currently available tend to stain the tooth structure a dark unaesthetic color and thus are unacceptable. However, the silver-containing sol-gel bioactive glass (Silver Theraglass®) containing compositions of the present invention retained a strong antibacterial effect, but surprisingly it did not stain the tooth structure. Additionally, the bioactive components served to rematerialize the dentinal tubules where many bacteria tend to colonize.

Tooth Resorption in Mammals:

Resorption of teeth can be a normal physiological process (exfoliation of primary teeth) or a pathological one. Causes of pathological resorption include pressure on the root (impacted tooth or expanding cyst or tumor), inflammation and infection (periodontal, apical, and internal resorption), orthodontic force, trauma and neoplasia, There is a very high incidence of tooth resorption in cats that are idiopathic, resembling the non-carious cervical tooth resorption seen in dogs, humans, and other species. These are unrelated to cervical lesions that are made by toothbrush abrasion seen in humans. Although tooth resorption in humans has been called many different terms they are often referred to as "invasive resorption," "idiopathic cervical resorption," and, more recently, "abfraction lesions." The veterinary medicine literature has also given them multiple labels over the years, as is common with lesions and syndromes that are poorly understood. Resorption of dental tissue occurs through the action of odontoclasts regardless of the initiating cause, and similar tooth resorption occurs in many different species including even humans.

A noncarious cervical lesion, or NCCL, is the loss of tooth structure at the cementoenamel junction, or CEJ, level that is unrelated to dental caries. Non-carious cervical lesions (NCCLs) are characterized by the loss of hard tissue at the cement-enamel junction (CEJ) in the absence of caries. These lesions, which can affect tooth sensitivity, plaque retention, caries incidence, structural integrity and pulpal vitality, are being seen with increasing frequency and present unique challenges for successful restoration. It is generally accepted that initiation and progression of NCCLs have a multi-factorial etiology, but the relative contribution of various processes still remain unresolved and a source of scientific debate. Several recent publications did not find evidence to support that the tissue loss of cervical enamel is produced by the abfraction mechanism. There is insufficient evidence concerning NCCLs to support the abfraction mechanism, the most widely accepted theory for these types of lesions in humans.

Domestic cats commonly suffer from external osteoclastic tooth resorption (FORL), a disease with many similarities to human multiple idiopathic root resorption. Invasive cervical resorption (ICR) is a clinical term used to describe an insidious and aggressive form of tooth resorption that can occur in any human tooth in the permanent dentition. Moreover, recent published studies have described human patients presenting with multiple Invasive Cervical Resorption (mICR), mICR is similar in characteristics to the feline disease FORL. It is interesting to note that a recent report in the American Journal of Veterinary Research found radiographic evidence of tooth resorption in over 90% of the 851 dogs that were examined.

Interestingly, domestic cats are the only animals known to suffer routinely from osteoclastic activity in the oral cavity, leading to a significant excess of resorption and loss of teeth. Domestic cats are unusual in that resorption of permanent teeth by osteoclasts is a very common condition. Epidemiological reports suggest that 72% of domestic cats suffer from the condition and the incidence of the disease increases with age. This disease in cats is known as "Feline Osteoclastic Resorptive Lesions" (FORL). It has been recently demonstrated that there are features of the feline CEJ and cervical root of the teeth that may be associated with increased rate of destruction by osteoclasts, including significantly reduced levels of mineralization of enamel and dentin, and thinner enamel and cementum. Studies have shown that the rate of osteoclastic resorption of calcified tissues is inversely proportional to mineral density.

The buccal surfaces of cat's teeth are reported to be most frequently affected, as has been described in epidemiological studies of feline osteoclastic lesions (FORL). It has been suggested that feline osteoclastic lesions may be a sequelae of periodontal disease, plaque accumulation, and inflammation, and that the buccal side bias in periodontal inflammation and plaque accumulation has been described previously in feline periodontitis. Self-cleansing of the lingual tooth surfaces by tongue movement is the most likely explanation.

The exposure of dentinal tubules, seen in a majority of early FORL lesions, suggests loss of cementum or enamel associated with trauma or periodontal disease. The CEJ structure has been shown to be significantly associated with resorptive lesions of the enamel margin and is frequently associated with exposed dentinal tubules.

FORL has become one of the most common dental diseases in cats. Dental resorptive lesions are also known by a variety of other names including odontoclastic resorptive lesions, feline neck lesions, cervical line lesions, chronic subgingival tooth erosions, feline external resorptive lesions, and/or subgingival resorptive lesions. This disease is characterized by cavitating lesions produced by osteoclastic (odontoclastic) resorption originating sub-gingivally and progressively eroding through the enamel/cementum and dentin layers into the pulpal tissues of the tooth. Odontoclasts are large multinucleated cells of up to about 400 nm in diameter and appear to be derived from the same lineage as osteoclasts, which are the cells responsible for bone resorption. The odontoclasts progressively attack apparently healthy tooth substance, producing large painful tooth lesions, ultimately resulting in tooth breakage with retention of root fragments in the gum.

Observation of dental resorptive lesions during routine examination of cats can be difficult because relatively little erosion of the cementum and enamel may be evident at the buccal surface. However, the lesion is apparent when examined radiographically. Although the lesion may not be obvious, it is commonly accompanied by signs of pain. Other clinical signs include anorexia, concurrent gingivitis, and excessive salivation.

The primary cause of dental resorptive lesions is not definitively known. Possible causes include oral inflammation, plaque, periodontal disease, systemic disease conditions, dietary factors, breed predisposition, and defects and diseases in the tissues of the tooth or periodontium. Of the studies done on feline dental resorptive lesions, the prevalence of the lesions consistently increases with age.

Currently, there is no effective treatment for dental resorptive lesions. Often, the affected teeth break off, thus creating the potential for root sequestrum formation and subsequent infection. Typically, affected teeth must be extracted because attempts to save the tooth by drilling out the lesion and filling it with restorative materials are ineffective. Approximately 90% of the repair attempts fall out within two years because of ongoing resorption. In addition, new lesions often develop in other teeth within the mouth of an affected individual.

Even though dental resorptive lesions are currently observed primarily in cats, there is the potential for the spread of this disease to other mammalian species, including, for example, dogs or other mammals including humans. For example, before the 1950s, the presence of feline dental resorptive lesions was extremely rare. However, recent studies have calculated prevalence rates of 28.5% to 57% in the last ten years.

FORL is one of the most common diseases in cats. Unlike, human cavities, the cause of FORL is unknown and there are currently no effective treatments for this feline disease. Specifically, cells known as odontoclasts (osteoclasts) are found in the defect causing tooth resorption. What exactly triggers this reaction has not been precisely determined, however, recent research has indicated that acidosis is a major regulator of osteoclastic formation and functional activity in the cat. It is suggested that local pH changes may play a significant role in the pathogenesis of FORL.

While normal tissue pH is around 7.5-9.0 (depending on the mammal), inflammation in the tissue can reduce the local pH to 5.5 or lower. However, it is important to note that the oral cavity of companion animals such as dogs and cats presents a very different environment than that of humans. The pH of human saliva is around 7.0 (neutral), whereas the saliva of cats and dogs is much more alkaline with a pH around 9.0. Additionally, dogs and cats cannot tolerate any dental product with a mint flavoring, whereas, humans prefer this flavoring in dental products. Xylitol is a common ingredient found in human dental products including toothpastes and mouthwashes due to its anti-cavity properties; however, xylitol has been shown to be toxic to dogs producing liver damage and anemia. Moreover, animals cannot expectorate dental product and therefore ingest all of the residual material. Although, little specific research has been performed as to the effects of fluoride on dog and cats, more care should be taken in the use of fluoride containing products in companion animals until its safe use has been established. The enamel thickness of dog and cat teeth is significantly thinner than that of human enamel. Human enamel is approximately 2.55 mm in thickness whereas cat enamel is on average 0.2 mm in thickness, and dog enamel is on average 0.5 mm in thickness. As far as dentin is concerned, the literature shows that there are more dentinal tubules per unit area in the cat and dog than in humans. Furthermore, the diameter of the dentinal tubules is smaller in the cat and dog than in humans.

In certain embodiments of the invention, bioactive glasses can increase the local oral pH upon exposure of the non-aqueous composition to an oral environment. Researchers consider that acidosis could be the locally acting exogenous factor that leads to the development of FORL, and contributes to the propensity of cat osteoclastic precursors to develop into large mature cells with high resorptive activity. Interestingly, the incidence of FORL is much higher today than it was in the 1950's. This may be due in part to diet acidification to control feline urologic syndrome. Recent research has shown that systemic acidosis causes increased osteoclastic activation and that loci of infection or inflammation in the cat oral cavity are likely to be acidic. It has been suggested that these local changes in pH (more acidic) may play a significant role in the pathogenesis of FORL. Cultures with primary osteoblasts have shown that bioactive glass stimulates the proliferation and differentiation of osteoblasts. Additionally, it has been demonstrated that the ionic species released during the dissolution of bioactive glass can increase osteoblastic proliferation. Without being limited by theory, it is believed that new tooth substance is formed by odontoblasts to heal the lesions. Thus, administration of a bioactive glass can therefore eliminate the need for tooth extraction and its associated complications.

Because it is estimated that greater than about 25% of cats seen by any given veterinarian for any given reason have dental resorptive lesions, what is desired in the art is a therapy to optimally inhibit the progression of clinically detectable, active dental resorptive lesions and to reduce the risk of the development of new lesions within the mouth of the affected individual. Also desired is a therapy to eliminate the need for tooth extraction and to alleviate the pain associated with dental resorptive lesions. It is desired that these therapeutics be used to both control the disease in cats and to reduce the risk of the spread or occurrence of dental resorptive lesions to other species, including humans.

Observation of dental resorptive lesions during routine examination of cats can be difficult because relatively little erosion of the cementum and enamel may be evident at the buccal surface. However, the lesion is apparent when examined radiographically. Although the lesion may not be obvious, it is commonly accompanied by signs of pain. Other clinical signs include anorexia, concurrent gingivitis, and excessive salivation (see, for example, Elizabeth M. Lund, et al., Prevalence and risk factors for odontoclastic resorptive lesions in cats, JAVMA, Vol. 212, No. 3, pp. 392-95 (Feb. 1, 1998)).

Dental resorptive lesions are distinguishable from other dental diseases, such as periodontal disease, dental caries, and alveolar bone loss. Periodontal disease and dental caries are caused by aggressive bacterial or microbial build-up due to poor oral hygiene, malocclusion, tartar build up, food impaction and faulty dental restorations (see, for example, Riviere et al., Infection and Immunity, 59(10), 3377-80 (1991), Reddy et al., J Periodontol, 211-217 (March 1995), and Weinreb et al., J. Periodont Res, 29, 35-40 (1994)). In periodontal disease, inflammation of the gum around the tooth results in leaching of the alveolar bone causing the teeth to become loose and to eventually fall out. In contrast, dental resorptive lesions can occur in the absence of periodontal disease and are caused by odontoclastic attack on the tooth surface itself, as opposed to the surrounding bone, as is the case with periodontal disease.

Periodontal Disease in Felines:

Periodontal disease as already noted, is common in the cat. Most cats require periodontal treatment by middle age. In fact, most require remedial therapy earlier in life. The accumulation of dental plaque on tooth surfaces incites inflammatory responses in the periodontium, resulting in gingivitis and periodontitis. Gingivitis is when the inflammation is limited to the gingiva; while periodontitis is when there is inflammatory destruction of the periodontal ligament and alveolar bone. Gingivitis is by definition reversible. Removal or adequate reduction of plaque will restore inflamed gingiva to health. Once clinically healthy gingival has been achieved, it can be maintained by daily removal or reduction of accumulated plaque. Home care is the most important aspect of treating periodontitis. Following professional therapy, cat owners most prevent or remove the accumulation of plaque on a daily basis. It is important to note that adult cats with established periodontitis will usually tolerate tooth brushing well.

Feline Gingivostomatitis:

Plaque control is the key to controlling. Feline gingivostomatitis is one of the most frustrating oral diseases seen in veterinary practice and presents with intra-oral inflammatory lesions. All breeds of cat can be affected at any age. This condition improves when plaque reduction efforts are made. A professional dental cleaning will transiently remove plaque, but tooth brushing is necessary to prevent daily plaque accumulation. Antibiotics provide transient improvement by decreasing the bacterial plaque burden, but long-term use promotes bacterial resistance. Currently available medical treatments include either drugs with poor chances of long-term success or drugs with undesirable or serious side effects (e.g. high-dose corticosteroids).

Bioactive Glass:

As noted above, the terms "bioactive glass" or "biologically active glass" are used interchangeably herein to refer to an inorganic glass material having an oxide of silicon as its major component and which is capable of bonding with growing tissue when reacted with physiological fluids. Such bioactive glass compositions will form a layer of hydroxycarbonate apatite in vitro when placed in a simulated body fluid.

Bioglass

One example of a bioactive glass suitable for use in the context of the present invention is a commercially available family of bioactive glasses, referred to in the art simply as "Bioglass", composed of $SiO_2$, $Na_2O$, $CaO$, and $P_2O_5$ in specific proportions. The proportions differ from the traditional soda-lime glasses in low amount of silica (less than 60 mol. %), high amount of sodium and calcium, and high calcium/phosphorus ratio. High ratio of calcium to phosphorus promotes formation of apatite crystals, wherein calcium and silica ions can act as crystallization nuclei Bioglasses are generally divided to two categories:

Class A bioglasses are osteoproductive. They bind with both soft tissues and bone. The HCA layer forms within several hours.

Class B bioglasses are osteoconductive. Bond to soft tissues is not facilitated. The HCA layer takes one to several days to form.

In the context of the present invention, Class A Bioglasses are more preferred. A detailed discussion of the various Bioglass compositions may be found at http://en.wikipedia.org/wiki/Bioglass#cite_note-biomat-0, the contents of which are incorporated by reference herein.

Particulate "Bioglass" materials suitable for us in the context of the present invention typically have the following composition by weight percentage:

TABLE 1

| Material | Weight Percent |
| --- | --- |
| $SiO_2$ | 40-60%, preferably 40-50% |
| CaO | 10-30%, preferably 20-25% |
| $Na_2O$ | 10-35%, preferably 20-25% |
| $P_2O_5$ | 2-8%, preferably 4-6% |

Some CaO can be replaced with MgO and some $Na_2O$ with $K_2O$ without much effect to bone bonding. Some CaO can be replaced with $CaF_2$ without altering bone bonding, this however modifies the dissolution rate of the glass. $B_2O_3$ or $Al_2O_3$ may be added for easier material processing, though they may influence the bone bonding. Alumina in particular inhibits bonding and thus its content should be restricted to small levels of about 1-1.5%.

TABLE 2

| Material | Weight Percent |
| --- | --- |
| MgO | 0-5% (optional) |
| $K_2O$ | 0-8% (optional) |
| $CaF_2$ | 0-25% (optional) |
| $B_2O_3$ | 0-10% (optional) |
| $Al_2O_3$ | 0-1.5% (optional) |

One particularly preferred composition of bioactive glass is sold under the name "Bioglass 45S5" and has the following characteristics:

TABLE 3

| Material | Weight Percent |
| --- | --- |
| $SiO_2$ | 45% |
| CaO | 24.5% |
| $Na_2O$ | 24.5% |
| $P_2O_5$ | 6% |

Theraglass®

A more preferred bioactive glass suitable for use in the context of the present invention is commercially available under the trade name Theraglass® and also includes Silver Theraglass® (Theraglass Limited, London, UK). Unlike the first generation of bioactive glasses described above, which are made using a very high temperature "melt" process, Theraglass® materials are made by a unique sol-gel process. Sol-gel glasses (like the Theraglass® line of products) can be formulated into, for example, ointments, creams, pastes, gels, and sprays. The regenerative nature of this material applies itself to the repair of teeth, bones, and skin, including soft tissue mucosa such as gingival tissue and periodontal ligaments). It is classified as a medical device ingredient and is able to provide a long lasting and strong antimicrobial effect and a barrier to infection. The sol gel process and resultant bioactive material gives a significant advantage in terms of versatility and corresponding uses. Theraglass® takes less energy and is less expensive to make. It is more uniform in consistency and can be controlled and adapted to the nano-level, thereby improving its performance for specific applications. For remineralization (HCA formation) it has been shown that 70% $SiO_2$ is optimal.

The morphology of the gel surface layer is a key component of the bioactive response. Studies on bioactive glasses derived from sol-gel processing have shown that such materials may contain significantly higher concentrations of SiO2 than traditional melt-derived bioactive glasses (e.g., on the order of 65% and higher) yet unexpectedly still maintain bioactivity (i.e., the ability to form a mineralized hydroxyapatite layer on the surface). While not wishing to be bound by theory, it has been proposed that the inherent porosity enables the retention, and indeed enhancement, of bioactivity.

The Theraglass® material may optionally include silver oxide ($Ag_2O$); such an embodiment is commercially available under the trade name Silver Theraglass®. Recent studies have shown that the introduction of silver oxide into bioactive glass compositions can minimize the risk of microbial contamination through the potential antimicrobial activity of the leaching Ag+ ions. More particularly, it has been shown that a bioactive glass composition doped with silver oxide elicits rapid bactericidal reaction. As noted above, the bioactive glasses produced by the sol-gel process are uniquely able to maintain bioactivity even with high concentrations of silicon oxide. Additionally, the sol-gel process permits the tailoring of the textural characteristics of the matrix, which, in turn permits the controlled time-release of powerful antibiotics like ionic silver. Thus, sol-gel process yields bioactive glass materials having a level and duration of antimicrobial and therapeutic activity that simply cannot be achieved with the melt-derived process.

Sol-gel produced Theraglass® has 2 or 3 components compared to the 4 components in melt-derived glasses. It has a strong ability to allow incorporation of other materials, and has a superior bioactivity level due to its greater surface area. The surface area of the sol-gel glasses is two orders of magnitude (i.e. 100 times) than that of the melt-derived glasses. An interconnected network of mesopores (2-50 nm) is responsible for the high surface area, which provides enhanced bioactivity. This increases effectiveness, e.g. only very small amount of material is required to achieve the therapeutic result. In addition, it is more porous, enabling other materials, proteins, or drugs (such as silver and zinc) to be incorporated into its structure and delivered in a time-release fashion. The ion release from sol-gel glasses such as Theraglass® occurs when it comes in contact with body fluids including saliva had gingival reticular fluids. This leads to the formation of hydroxyl carbonate layer (HCA) on protein containing surfaces such as teeth and mucosal tissues. In addition, it stimulates bone to heal (by up-regulating bone cell forming genes). It has been shown to be safe, and if it enters the body it is resorbed and harmlessly excreted.

Silver Theraglass® has very strong antimicrobial properties arising through the action of silver, attributed to the significant surface area of the material, combined with the healing properties of the bioactive glass. The silver is released over time thereby providing lasting protection. See Saravanapavan P. et al, "Binary Cao-Sio(2) Gel-Glasses For Biomedical Applications" Biomed Mater Eng. (2004) Vol. 14, No. 4, pp. 467-86.

Particulate "Theraglass" materials suitable for us in the context of the present invention typically contain at least 50%, more preferably at least 60%, even more preferably at least 70% silicon oxide ($SiO_2$). Components such as silver and/or zinc, as well as CaO, MgO, $CaF_2$, $Na_2O$, $K_2O$, $P_2O_5$, $B_2O_3$, $Al_2O_3$, may also be included, within ranges similar to those utilized by the melt-derived bioglass materials. One of skill in the art may readily determine the optimal weight percentages of these additional ingredients.

Bisphosphonates:

Bisphosphonates are known in the art to bond to hydroxyapatite in bone and to inhibit the bone resorptive activity of osteoclasts (see, for example, H. Fleisch, Bisphosphonates In Bone Disease, From The Laboratory To The Patient, 3rd Edition, Parthenon Publishing (1997)). For example, bisphosphonates are known to be useful in the treatment of such diseases as osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption and bone formation. Even though bisphosphonates have been used to treat the above-mentioned diseases, they have not been used to treat dental resorptive lesions.

Topical bisphosphonates are anti-osteoclastic agents. Examples of such bisphosphonates include, for example, alendronate, cimadronateclodronate, tiludronate, etidronate, ibandronate, neirodronate, olpandronate, risedronate, piridronate, zoledronate, pharmaceutically acceptable salts thereof, and mixtures thereof. Those of ordinary skill in the art will appreciate that there are other appropriate anti-orthoclastic agents.

It is surprisingly been found in the present invention that bisphosphonates are effective for inhibiting, i.e. treating and reducing the risk of contracting, dental resorptive lesions. Without being bound by theory, it is believed that new tooth substance is formed by odontoblasts to heal the lesions. Thus, administration of a bisphosphonate can eliminate the need for tooth extraction and its associated complications.

It is also surprisingly found in the present invention that a therapeutically effective amount of a bisphosphonate can be selectively delivered to the subgingival tooth surface and alveoli dentales such that at about 24 hours after administration the resulting average concentration of the bisphosphonate at the subgingival tooth surface and alveoli dentales is at least about two times greater than the average concentration in the skeleton, for example at the diathesis of the femur.

Bioactive Compositions of the Present Invention:

As noted above, the present invention relates to the unexpected discovery that the combination of micron-sized particulates bioactive glass, including dentinal tubule-occluding particulates, and a topical bisphosphonate yields a composition that is capable of treating and/or preventing a wide range of dental pathologies and augmenting the natural healing process. While not being bound to any particular theory or mechanism, it is believed that the high surface area and reactivity of particulate bioactive glass provides for a release of sodium (a component found in many bioactive glasses) which increases pH and increases oxygen in the lesion which otherwise has a lower pH. This has a bacteriostatic effect and permits the bisphosphonate to function by activating various growth factors implicated in tissue repair. These reactions cause a higher negative surface charge on the glass surface and the development of a high specific surface area (e.g. from 0.5 m2/g initially to over 50 m2/g by 12 hours) that attracts collagen, fibronectin and cells. Moreover, the bioactive glass provides for the precipitation of calcium and phosphorus naturally present in the wound exudates and blood, which causes the rapid formation of a calcium and phosphate layer that, may incorporate collagen, fibrin and fibronectin to stabilize the lesion.

The bioactive glass/bisphosphonate compositions of the present invention are most effective when sized to enter the exposed dentinal tubules (i.e., characterized by dentinal tubule-occluding particles that immediately and effectively occlude tubules, in and of themselves). In small animals, such as cats, the dentinal tubule diameter is on the order of 1 to 5 microns. Accordingly, the preferred particle size for the bioactive glass less than 10 microns, preferably less than 5 microns, more preferably less than 2 microns can also be used. Particles of such a small size range generally provide for the advantages of the present invention without any undesirable immune response.

As discussed in greater detail in the next section, the active agents, bioactive glass and bisphosphonate, can be combined in any pharmaceutically acceptable carrier to facilitate application to the teeth and surrounding tissues. The resulting formulations may take the form of a solid, liquid, paste or gel, depending on the desired administration route. For example, the compositions of the present invention may be formulated the present invention can be combined with an ointment, white petrolatum, mineral oil, glycerin, and other vehicle known to those of ordinary skill in the art. Alternatively, the formulations may be nutraceutically formulated, together with food, supplements, chew sticks or other veterinary products including tooth pastes and dental prophylaxis pastes.

Administration and Dosage:

When administering active agents of the present invention as a dental, pharmaceutical or nutraceutical composition formulated for administration to small mammals, including without limitation, mice, rats, hamsters, guinea-pigs, rabbits, cats, and dogs, the agents can be directly or topically administered, either singly or in a cocktail combination, or alternatively can be formulated into a dosage form using known pharmaceutical and/or nutraceutical preparation methods. For example, according to the needs of the subject, the compositions of the present invention can be made into an external preparation, for example, a liniment or a poultice, by admixing it with a suitable base material that is inactive against the active agent(s). Alternatively, the active agents of the present invention or pharmaceutical formulations thereof can take the form of an orally administrable elixir, solution or suspension, with water or any other pharmaceutically acceptable liquid. Likewise, the active agents can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, adhesives, and such, in a unit dose form required for generally accepted drug implementation. The amount of active ingredient contained in such a preparation makes a suitable dosage within the indicated range acquirable. The active agents may be utilized in their native state or in the form of a pharmaceutically acceptable salt thereof.

The active agents of the present invention can be administered to the subject by direct application onto the ailing site, for example by selective delivery to the sub-gingival tooth surface and gingival sulcus. Alternatively, in the context of the treatment and prevention of dental resorptive lesions, it may be desirable to administer the active agents throughout the mouth, both above and below the gum line. Particles may adhere to tooth surfaces and become trapped within the exposed dentinal tubules for an extended period of time, continuing to release sodium, calcium, and phosphate ions to immediately occlude the exposed and patent dentinal tubules, maintain elevated pH at the tooth surface and foster remineralization over time.

In contrast to previous processes, such as that described by Salonen et al. in U.S. Pat. No. 5,891,233 that require the active ingredients to be protected by use of a "periodontal pack" for up to a week, the present invention does not require any type of packing as the particles immediately occlude the opened dentinal tubules and are therefore protected by the tubules themselves.

The present invention also contemplates the combination of bioactive glass and bisphosphonate of the present invention with other treatments or dressings, such as sodium fluoride cellulosic, synthetic and other dressings/treatments known to those of ordinary skill in the art. Dressings fiberglass made from fibers of bioactive glass can also be used.

It has been determined most preferable to mix the particulate bioactive glass and the bisphosphonate of the present invention is just prior to application to the lesion. If the two are mixed well prior to application, e.g. one week, the effectiveness of the composition may be compromised. Accordingly, the present invention is also directed to the incorporation of the bioactive particulate glass and at least one bisphosphonate in a two-part system wherein the bioactive glass and bisphosphonate are mixed and simultaneously applied. For example, a two-part mixing syringe with two separate storage chambers and a mixing chamber can be used. Other two-part system s could also be used. For example, the particulate bioactive glass can be incorporated into a bandage and the topical bisphosphonate can be applied to the lesion that is followed by application of the bandage. Other two-part delivery systems are known to those of ordinary skill in the art. Alternatively, the bioactive glass may itself be added to an electrostatically-charged wax barrier sealant, such as OraVet Barrier Sealant, and applied to the subject's teeth as a therapeutic addition to the barrier material that provides a physical barrier against plaque. Since it is very costly to do a prophylaxis on a dog or cat, the wax is preferably applied in a veterinarian's office and refreshed weekly at home by the animal's owner. It is very easy to apply, sticks to the teeth, and wears off over time. The addition of a bioactive glass to this material would make it an ideal therapeutic agent for cats, dogs as well as humans who are physically and/or mentally compromised and cannot care for their own teeth because of their disability.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Materials and Methods

Canine Teeth

Figure 2:
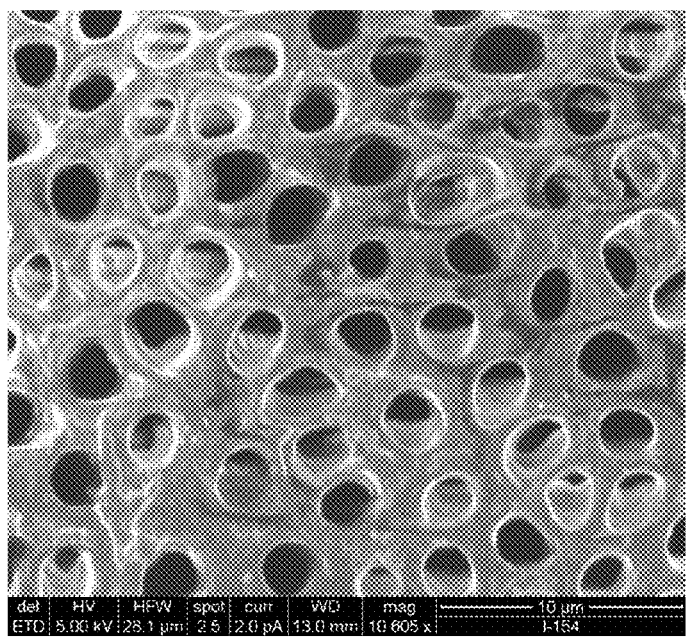
FIG. 2 depicts a dog dentin control surface that has been treated with 37% phosphoric acid for 30 seconds to remove any smear layer after sectioning and grinding to open the dentinal tubules emulating clinical sensitivity and FORL. The surface has not been treated with bioactive glass in accordance with the present invention (10,605× magnification).
Figure 3:
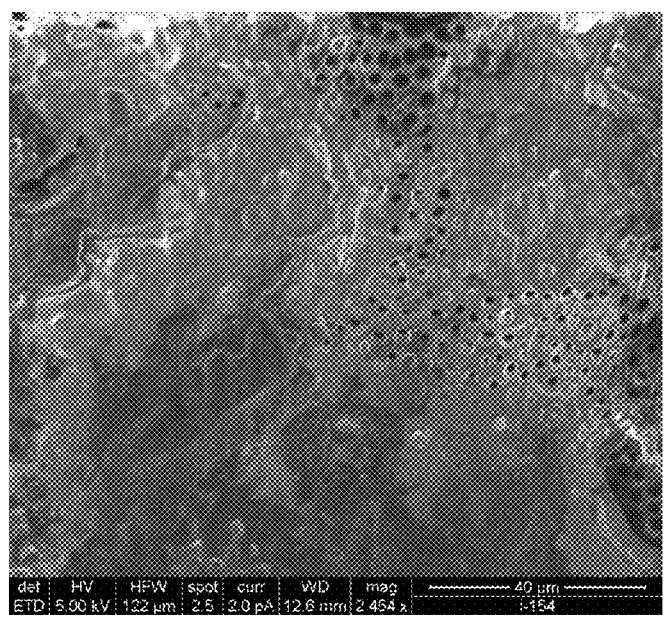
FIG. 3 depicts a dentin surface that has been treated with an acid etch to open the dentinal tubules emulating tooth sensitivity and FORL and then treated with a bioactive glass composition in accordance with the present invention in water and glycerin for 2 minutes (Particle size range 1-16 microns, 2,454× magnification).
Figure 4:
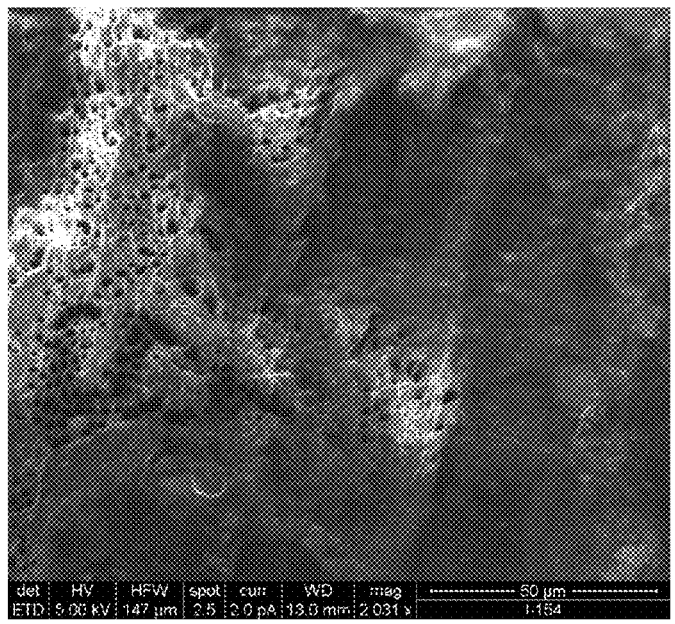
FIG. 4 depicts a dentin surface that has been treated with an acid etch to open the dentinal tubules emulating tooth sensitivity an FORL and then treated with a bioactive glass composition in accordance with the present invention in water and glycerin for 2 minutes (Particle size range 1-16 microns, 2,031× magnification).
Figure 5:
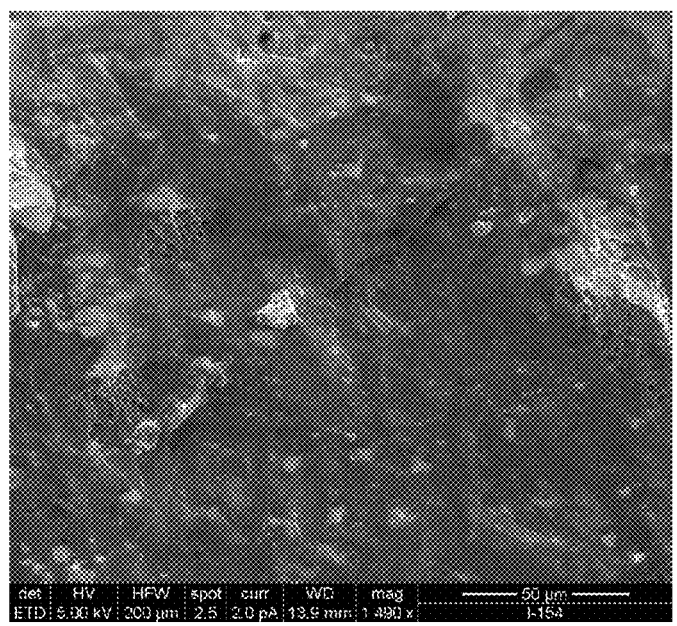
FIG. 5 depicts a dentin surface that has been treated with an acid etch to open the dentinal tubules emulating tooth sensitivity and FORL and then treated with a bioactive glass composition in accordance with the present invention in water and glycerin for 2 minutes (Particle size range 1-16 microns, 1,490× magnification).
Figure 6:
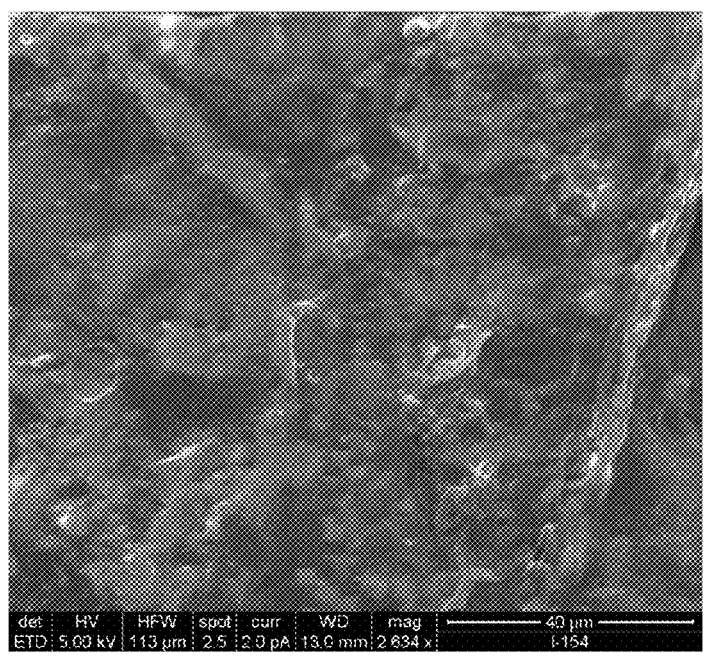
FIG. 6 depicts a dentin surface that has been treated with an acid etch to open the dentinal tubules emulating tooth sensitivity and FORL and then treated with a bioactive glass composition in accordance with the present invention in water and glycerin for 2 minutes (Particle size range 1-16 microns, 2,634× magnification).
Figure 7:
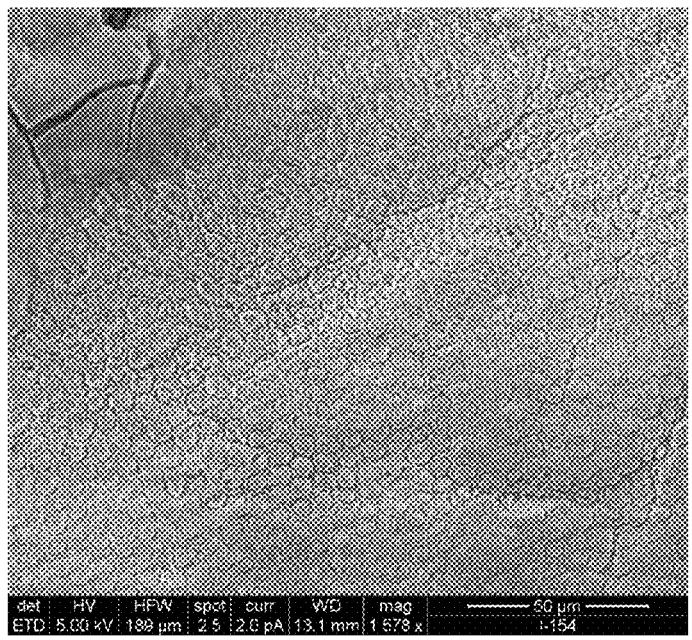
FIG. 7 depicts an area of a feline tooth afflicted with resorptive lesion (FORL). Notice breakdown of surface on the upper left corner at Cemento-enamel junction (CEJ) with exposure of underlying dentin. 4,016× magnification.

In vitro experiments were performed using sections of extracted canine teeth. These teeth had been previously extracted by a veterinarian for medical reasons, because of advanced periodontal disease and/or tooth decay. The sections were cut from the extracted dog teeth using a diamond saw. The sections of cut teeth were approximately 1.0 mm thick and of the appropriate size necessary for Scanning Electron Microscopic (SEM) examination. The top surface of the sections (non-pulpal side) were ground on a series of wet silicon-carbide papers ranging from 320 to 600-grit. This sanding procedure was done in order to standardize the test surfaces. The surfaces were then treated with 37% phosphoric acid for 30 seconds to remove any smear layer created during the grinding process, and to expose the underlying dentinal tubules (see FIGS. 1 and 2). The surface was rinsed with a gentle stream of distilled water for 10 seconds, and then gently dried with a stream of oil-free air. Each tooth section was split in half and the experimental material was applied on one-half of the specimen as described in the examples. The untreated half of the cut section with evident dentinal tubules is shown in FIGS. 1 and 2. Scanning Electron Microscopy (SEM) was performed on the tooth sections. The sections were mounted on SEM stubs using adhesive tape. All specimens were dried and examined in a Quanta 200 Scanning Electron Microscope.

Feline Teeth

In vitro experiments were performed extracted feline teeth with resorptive lesions. These teeth had been previously extracted by a veterinarian for medical reasons, because of Feline Osteoclastic Resorptive Lesions (FORL. Scanning Electron Microscopy (SEM) was performed on the feline teeth. The feline teeth were mounted on SEM stubs using adhesive tape. All feline teeth were dried and examined in a Quanta 200 Scanning Electron Microscope. Randomly selected feline teeth with evidence of FORL lesions were treated with the experimental compositions before SEM examination

Example 1

Dentinal Tubule Occlusion

Herein, the effectiveness of a bioactive glass composition in occluding dentinal tubules was tested. The experimental treatment composition was a mixture containing a bioactive glass composition such as described above in Table 2, including Silicon Oxide (45%), Calcium Oxide (24.5%), Sodium Oxide (24.5%), and Phosphorous Oxide (6%). The mixture was melted in a covered platinum crucible at 1,350 C.° for 2 hours in order to achieve homogenization. The mixture was later quenched in deionized water at 0 C.°. Fritted glass was placed in an appropriate milling apparatus, such as a ball mill or impact mill. The glass was milled for 2 hours and separated into appropriate size ranges. This process yielded glass particulates on the order of 1-16 microns, as confirmed by scanning electron microscopy. The resulting compositions were used to treat the dentin sections previously described.

The exposure times of the experimental composition on the dentinal surfaces varied between two minutes with scrubbing to 3 days with no agitation. The occlusion of the tubules is evident in FIGS. 3-7. Visible in FIGS. 3-7 are total and partial occlusion of the dentin tubules with multiple sizes of small particles present, in particular the effective dentinal tubular occluding particles. In addition, the larger visible particles act as reservoirs for the chemical composition. Early formation of hydroxyapatite crystals beginning on the dentin surface was confirmed by FTIR.

Example 2

Treatment of FORL

Figure 8:
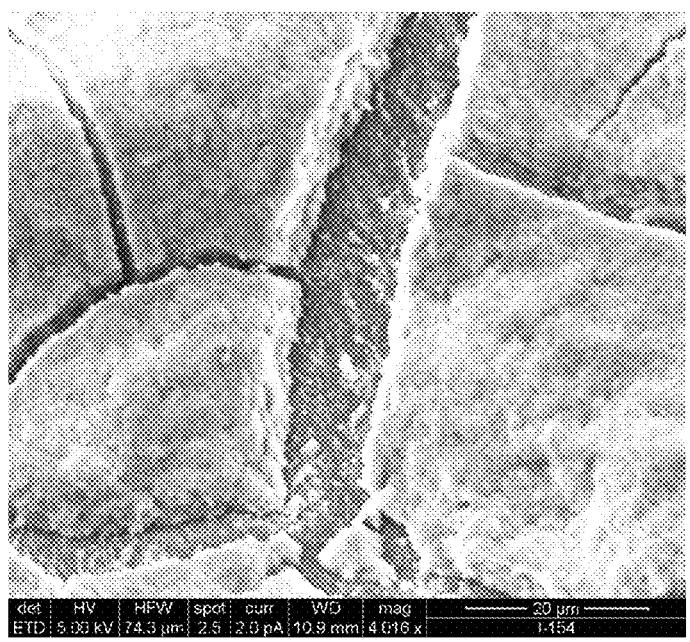
FIG. 8 depicts an area of a feline tooth afflicted with resorptive lesion (FORL). Notice breakdown of surface with exposure of underlying dentin. 4,016× magnification.
Figure 9:
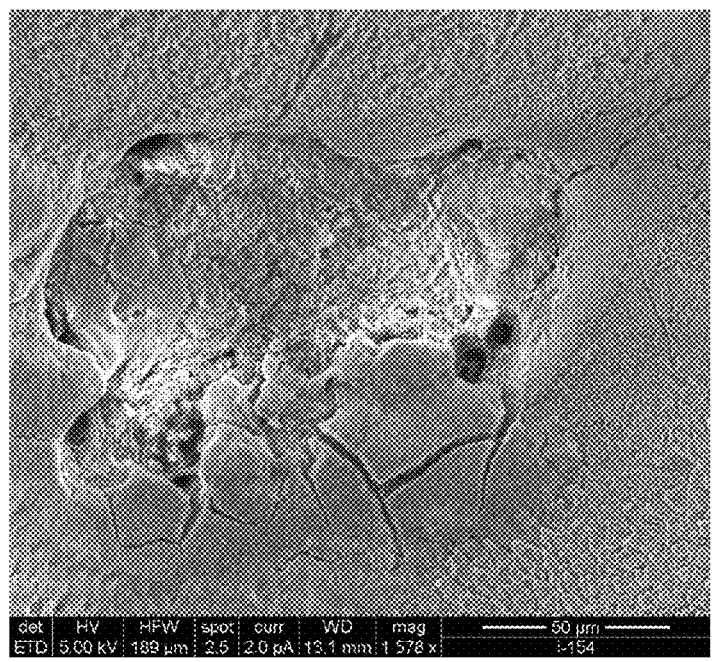
FIG. 9 depicts an area of a feline tooth afflicted with resorptive lesion (FORL). Notice severe breakdown of surface with exposure of underlying dentin. 4,016× magnification.

FIGS. 8 and 9 indicate the results obtainable by using submicron particles made in accordance with Example 1, in the context of treating resorptive lesions in feline teeth. With the lack of large particles for reservoir activity, there was less complete regeneration as confirmed by FTIR.

Example 3

Particle Sizes

The composition of the starting product for the following examples was the same as Example 1 with the use of a fluoride-containing bioactive glass. The mixture was poured into a slab, allowed to cool to room temperature and crushed. Crushed glass fractions were then separated by sieving through a standard screen. Fractions were then separated and retained. This process yielded particles on the order of 1-16 microns, as confirmed by scanning electron microscopy. These mixtures were used to treat the dentin sections previously described.

Bioactive glass samples containing 45% silicon oxide were utilized in the preparations with the same results seen in Example 1. Again, the key to these data was the presence of the sized range of particles. Present in these examples are ranges up to 60% silica with a size range in particles ranging from 1-16 micron.

Example 4

Clinical Trials

A split-mouth experimental design was used in in vivo clinical trials. The teeth on the left side of the animal's mouth were treated with the normally used prophylaxis paste containing fluoride (Zircon) and served as the control side. The teeth on the right side of the animal's mouth were treated with the above-described experimental compositions. The above experimental compositions, including the fluoride-containing bioactive glass compositions, were used as the prophylaxis paste (in place of the normally used Zircon paste) during routine dental hygiene prophylaxis on a group of cats and dogs seen in a standard veterinary practice. After scaling and root planning, the teeth were polished with the Zircon paste or the experimental prophylaxis paste using a standard dental hand piece with a rotary rubber prophylaxis cup, as normally done in a standard veterinary practice.

Standard veterinary oral examinations were performed on all animals at the start of the trials, and at 6-week intervals for a total of 18 months. Included in the oral examinations were periodontal status (periodontal probing measurements, evidence of periodontal disease, gingival inflammation, swollen gingival tissue, gingival bleeding upon probing, gingival hyperplasia, evidence of resorptive lesions/FORL (feline caries) or dental decay in the dogs.

Example 5

Effect of Particle Size on pH

The antimicrobial effect of calcium hydroxide is related to the release of hydroxyl ions in an aqueous environment that produces an elevated pH of 12.5. It has been widely used in endodontic therapy since its introduction in 1920. However, calcium hydroxide can weaken the dentin structure, and alternative antibacterial endodontic agents have been recently sought. Previous work in other labs has shown that bioactive glass materials have interesting antibacterial properties similar to calcium hydroxide, and thus have been suggested as topical root canal disinfectants. Bioactive glass has the additional advantage of bioactivity, including the induction of dentin mineralization. It has been reported that suspension supernatants of micrometric (100 um) bioactive glass attained a pH of 8.3 after 10 minutes, whereas a pH of 11.7 was similarly achieved with nanometric (20-60 nm) bioactive glass. Thus, it has been suggested that by decreasing the size of the bioactive glass particles, a pH elevation of over three units can be achieved, due to the increase of the specific surface area and the release of more alkaline species.

The in vitro behavior of Bioglass 45S5 was investigated herein. The "45S5" name signifies glass with 45 wt. % of $SiO_2$ and 5:1 ratio of CaO to $P_2O_5$. Lower Ca/P ratios do not bond to bone. The key composition features of Bioglass is that it contains less than 60 mol % $SiO_2$, high $Na_2O$ and CaO contents, high CaO/$P_2O_5$ ratio, which makes Bioglass highly reactive to aqueous medium and bioactive. Bioglass 45S5 with five particle size distributions was studied by measuring the in situ pH after immersion in an aqueous physiologic saline. As discussed in greater detail below, an immediate and sustained elevation in pH was observed regardless of particle size.

TABLE 4

| Average Particle Size | pH (reached within 30 seconds) | Observation |
|---|---|---|
| 100 um | 11 | Higher than the pH of 8.3 observed by others after 10 minutes. |
| 16 um | 12.7 | Higher than nanometric pH. |
| 5 um | 13.02 | Higher than calcium hydroxide pH. |
| 2 um | 12.6 | Higher than nanometric pH. |

It has been suggested that by decreasing the size of the Bioglass particles, a significant increase in pH can be achieved, due to the increase of the specific surface area and the release of more alkaline species. Accordingly, the ability of aqueous Bioglass 45S5 suspensions, utilizing an array of particle sizes, to raise the local pH was assayed via microvolt measurements. Different particle sizes of Bioglass 45S5 were used: 300-500 um, 100-300 um, <100 um, 16 um, 5 um. Time vs. maximum pH was measured, as well as plateau duration. Suspension supernatants (1:10 wt/wt) of micrometric (100 um) BG evidenced a pH of 8.3 after 10 minutes, whereas a pH of 11.7 was similarly achieved with nanometric (20-60 nm) BG. Unexpectedly, it was discovered that micron-sized particles of Bioglass 45S5 produced an immediate and sustained elevation in pH. The pH change has been previously shown to vary depending on the surface area to volume ratio, sample dosage. By studying the pH changes in the solution, a fast and simple determination of the in vitro behavior of the glass can be determined.

INDUSTRIAL APPLICABILITY

The present invention demonstrates the utility of micron-sized particular bioactive glass compositions in the treatment and prevention of dental diseases, such as periodontal disease, tooth decay and tooth resorption, in domesticated animals, particularly small companion animals such as dogs and cats. Given that these maladies are associated with premature morbidity and mortality, the herein described composition and care methods may significantly improve the quality of life for these animals by many years.

All patents and publications referred to herein are incorporated by reference to the same extent as if each individual publication was specifically and individually indicated as having been incorporated by reference in its entirety.

While the invention has been described in detail and with reference to specific embodiments thereof, it will be apparent to one skilled in the art that various changes and modifications can be made therein without departing from the spirit and scope of the invention.

What is claimed:

1. A composition for the treatment of dental pathology in a mammal, said composition comprising a therapeutically effective amount of micron-sized dentinal tubule-occluding particulates of a sol-gel derived or melt-derived bioactive glass having an average particle size of less than 10 microns, wherein said bioactive glass consists of:
   a. 40 to 60 wt % $SiO_2$ if melt-derived or at least 65 wt % $SiO_2$ if sol-gel derived;
   b. 10 to 30 wt % CaO, 0 to 5 wt % MgO, and/or 0 to 25 wt % $CaF_2$;
   c. 10 to 35 wt % $Na_2O$ and/or 0 to 8 wt % $K_2O$;
   d. 2 to 8 wt % $P_2O_5$;
   e. 0 to 10 wt % $B_2O_3$
   f. 0 to 1.5 wt % $Al_2O_3$
   g. 0 to 15 wt % silver oxide; and
   h. at least one bisphosphonate.

2. The composition of claim 1, wherein said bioactive glass contains 0.1 to 15% by weight silver oxide.

3. The composition of claim 1, wherein said at least one bisphosphonate is selected from the group consisting of alendronate, cimadronate, clodronate, tiludronate, etidronate, ibandronate, neirodronate, olpandronate, risedronate, piridronate, and zoledronate.

4. The composition of claim 1, wherein said bioactive glass has an average particle size of less than 5 microns.

5. The composition of claim 1, wherein said bioactive glass has an average particle size of less than 2 microns.

6. The composition of claim 1, wherein said bioactive glass is a melt-derived glass that contains 40-60% by weight $SiO_2$, 10-35% by weight $Na_2O$, 10-30% by weight CaO, and 2-8% by weight $P_2O_5$.

7. The composition of claim 1, wherein said bioactive glass is a sol-gel derived bioactive glass that contains at least 70 wt % silicon oxide and 0.1 to 15% by weight silver oxide.

8. A formulation suitable for topical administration to the oral cavity, including the visible tooth surface, the sub-gingival tooth surface and the gingival sulcus, said formulation comprising the composition of claim 1 as an active agent in combination with one or more pharmaceutically or nutraceutically acceptable carriers.

9. The formulation of claim 8, wherein said formulation takes the form of a solid, semi-solid, gel, paste, liquid, solution, or suspension.

10. The formulation of claim 8, wherein said nutraceutically acceptable carrier is selected from the group consisting of foods, supplements, and chew sticks.

11. A method of treating and/or reducing the risk of developing a dental pathology in a non-human animal subject in need thereof, said method comprising the step of administering to said subject an amount of the composition of claim 1 sufficient to immediately and effectively occlude the dentinal tubules in said non-human animal subject.

12. The method of claim 11, wherein said non-human animal is a companion animal and said dental pathology is selected from the group consisting of resorptive lesions, plaque accumulation, periodontal disease, gingivitis, periodontitis inflammation, exposed and opened dentinal tubules, dentinal hypersensitivity, cavities, and tooth decay.

13. The method of claim 11, wherein said administration step comprises (a) topically formulating said composition in combination with a pharmaceutically or nutraceutically acceptable carrier or media suitable for veterinary application and (b) directly applying said topical formulation to the visible tooth surface, the sub-gingival tooth surface and the gingival sulcus.

14. The method of claim 11, wherein the bioactive glass of said composition contains 0.1 to 15% by weight silver oxide.

15. The method of claim 11, wherein the at least one bisphosphonate is selected from the group consisting of alendronate, cimadronate, clodronate, tiludronate, etidronate, ibandronate, neirodronate, olpandronate, risedronate, piridronate, and zoledronate.

16. The method of claim 11, wherein said bioactive glass has an average particle size of less than 5 microns.

17. The method of claim 11, wherein the bioactive glass of said composition has an average particle size of less than 2 microns.

18. The method of claim 11, wherein the bioactive glass of said composition is a melt-derived bioactive glass that contains 40-60% by weight $SiO_2$, 10-35% by weight $Na_2O$, 10-30% by weight CaO, and 2-8% by weight $P_2O_5$.

19. The method of claim 11, wherein the bioactive glass of said composition is a sol-gel derived bioactive glass that contains at least 70 wt % silicon oxide and 0.1 to 15% by weight silver oxide.

20. A method of treating and/or reducing the risk of developing non-carious cervical lesions (NCCL) in a human subject in need thereof, said method comprising the step of administering to said subject the composition of claim 1.

21. The method of claim 20, wherein the bioactive glass of said composition contains 0.1 to 15% by weight silver oxide.

22. The method of claim 20, wherein the at least one bisphosphonate is selected from the group consisting of alendronate, cimadronate, clodronate, tiludronate, etidronate, ibandronate, neirodronate, olpandronate, risedronate, piridronate, and zoledronate.

23. The method of claim 20, wherein the bioactive glass of said composition has an average particle size of less than 5 microns.

24. The method of claim 20, wherein the bioactive glass of said composition has an average particle size of less than 2 microns.

25. The method of claim 20, wherein the bioactive glass of said composition is a melt-derived glass that contains 40-60% by weight $SiO_2$, 10-35% by weight $Na_2O$, 10-30% by weight CaO, and 2-8% by weight $P_2O_5$.

26. The method of claim 20, wherein the sol-gel derived bioactive glass of said composition contains at least 70 wt % silicon oxide and 0.1 to 15% by weight silver oxide.

* * * * *